US 7,462,347 B2

(12) United States Patent
Gray

(10) Patent No.: US 7,462,347 B2
(45) Date of Patent: Dec. 9, 2008

(54) FLUORESCENT MEMBRANE INTERCALATING PROBES

(75) Inventor: Brian D. Gray, Wayne, PA (US)

(73) Assignee: Phanos Technologies, Inc., Culver City, CA (US)

( * ) Notice: Subject to any disclaimer, the term of this patent is extended or adjusted under 35 U.S.C. 154(b) by 101 days.

(21) Appl. No.: 11/346,554

(22) Filed: Feb. 3, 2006

(65) Prior Publication Data

US 2006/0193780 A1   Aug. 31, 2006

Related U.S. Application Data

(63) Continuation of application No. 10/220,241, filed as application No. PCT/US01/06923 on Mar. 5, 2001, now abandoned.

(60) Provisional application No. 60/186,682, filed on Mar. 3, 2000.

(51) Int. Cl.
*A61B 10/00* (2006.01)
*A61B 5/00* (2006.01)
*A61B 8/00* (2006.01)

(52) U.S. Cl. ........................ 424/9.6; 424/1.11; 424/1.65; 424/9.1; 548/400

(58) Field of Classification Search ................ 424/1.11, 424/1.37, 1.65, 9.1, 9.3, 9.4, 9.5, 9.6, 9.7, 424/9.8; 548/146, 215, 300.1, 400; 430/581
See application file for complete search history.

(56) References Cited

U.S. PATENT DOCUMENTS

| | | | | |
|---|---|---|---|---|
| 4,762,701 A | * | 8/1988 | Horan et al. | 424/1.17 |
| 4,783,401 A | * | 11/1988 | Horan et al. | 435/34 |
| 4,859,584 A | * | 8/1989 | Horan et al. | 435/29 |
| 5,665,328 A | * | 9/1997 | Horan et al. | 424/1.17 |
| 5,667,764 A | * | 9/1997 | Kopia et al. | 424/1.45 |
| 5,804,389 A | * | 9/1998 | Tada | 435/7.1 |
| 5,968,479 A | | 10/1999 | Ito et al. | |
| 6,004,536 A | * | 12/1999 | Leung et al. | 424/9.6 |
| 6,027,709 A | | 2/2000 | Little et al. | |

FOREIGN PATENT DOCUMENTS

| | | |
|---|---|---|
| EP | 0 800 831 A1 | 10/1997 |
| WO | WO 89/10758 A1 | 11/1989 |

* cited by examiner

*Primary Examiner*—D. L Jones
(74) *Attorney, Agent, or Firm*—Rothwell, Figg, Ernst & Manbeck PC

(57) ABSTRACT

The invention relates to a family of cyanine dyes which fluoresce in the far red and near infra red wavelengths of the spectrum and preferably possess lipophilic side chains. The dyes of the invention are soluble in commercially available membrane staining vehicles, are useful as probes for rapidly staining lipophilic structures such as membranes in cells or isolated from cells, and are well retained therein. Methods of using the dyes to detect stained cells both in vivo and in vitro are also disclosed.

12 Claims, No Drawings

FLUORESCENT MEMBRANE INTERCALATING PROBES

CROSS REFERENCE TO RELATED APPLICATION

The present application is a continuation of application Ser. No. 10/220,241 filed Nov. 12, 2002 now abandonded, which was the national stage of International Application No. PCT/US01/06923 filed Mar. 5, 2001, which claims the benefit of application Ser. No. 60/186,682 filed Mar. 3, 2000.

STATEMENT REGARDING FEDERALLY SPONSORED RESEARCH OR DEVELOPMENT

This invention was made with United States Government support under grant number R43 CA86692 awarded by the National Cancer Institute, NCI and grant number R44 EB00228 awarded by the National Institute of Biomedical Imaging and Bio Engineering, NBIB. Accordingly, the United States Government may have certain rights in this invention.

FIELD OF THE INVENTION

The present invention relates to fluorescent, membrane intercalating compounds useful as dyes and probes. More particularly, the invention relates to lipophilic fluorescent compounds with an increased signal to noise ratio that are useful for rapidly labeling a variety of lipophilic particles or objects containing lipophilic structures, including cells, liposomes, microspheres and virus particles.

DESCRIPTION OF THE RELATED ART

It is known that fluorescent dyes have many uses and are particularly suitable for biological applications in which the high sensitivity detection of fluorescence is desirable. By binding to a specific biological ingredient in a sample, a fluorescent dye can be used to indicate the presence or the quantity of the specific ingredient in a sample. A variety of fluorescent dyes is available for fluorescent staining and such dyes are employed in quantitation of, e.g., cells, proteins, DNA and RNA. Fluorescent dyes are also employed for monitoring cellular trafficking in response to various physiological conditions. Such dyes have a wide range of applicability in both clinical and research applications where cell sorting and monitoring of cellular trafficking, proliferation and other responses are desired.

Fluorescent dyes are known to be particularly suitable for biological applications in which a highly sensitive detection reagent is desirable. Dyes that are able to preferentially bind to a specific biological ingredient or component in a sample enable the observer to determine the presence, quantity or location of that specific ingredient or component. In addition, specific biological systems can be monitored with respect to their spatial and temporal distribution in diverse environments. Cyanines are particularly advantageous for such applications, due to their high extinction coefficients and their amenability to the systematic selection of structural variations which give predictable shifts in excitation and emission properties. As a result, cyanine dyes have been used in various biological applications. The use of certain cationic lipophilic cyanine dyes, including $DiIC_{18}$, $DiOC_{18}$ and their $C_{12}$ to $C_{22}$ homologs in combination with an osmolarity regulating agent to stain cells for the purposes of labeling viable cells, tracking stained cells in vivo, and measuring cell growth rate has been previously described.

U.S. Pat. No. 4,762,701, which is incorporated herein by reference, refers to in vivo methods for tracking cyanine labeled cells that fluoresce in the visible regions of the spectrum and for determining cell lifetimes by measuring the rate at which the dye in labeled cells administered to a subject disappear.

U.S. Pat. No. 4,783,401, which is incorporated herein by reference, refers to methods for labeling viable cells with cyanine dyes that fluoresce in the visible regions of the spectrum in order to, among other things, measure the growth rate of cultured cells.

U.S. Pat. No. 4,859,584, which is incorporated herein by reference, refers to methods for determining the growth rate of cyanine labeled cells that fluoresce in the visible regions of the spectrum growing in vitro and in vivo.

U.S. Pat. No. 5,804,389, which is incorporated herein by reference, refers to methods for determining abnormal cell shedding rates by labeling cell membranes with cyanine dyes that fluoresce in the visible regions of the spectrum and observing the rate at which the labeled cells are shed from the mucosal surface.

U.S. Pat. No. 6,004,536 to Leung et al., which is also incorporated by reference herein, refers to cyanine dyes possessing two lipophilic alkyl chains that are preferably equal in length and incorporate either a reactive functional group, or a phenyl, sulfo, sulfophenyl, or a bromo or chloro substituent that are useful for staining lipophilic structures, such as membranes in cells or tissues, membranes isolated from cells, natural or artificial liposomes, lipoproteins or polymers. Leung et al. states that the dyes are preferably soluble in an aqueous environment.

Flow cytometry and fluorescence activated sorting have been used extensively to separate different classes of cells in the cell populations in blood and in bone marrow. Such methods have been particularly useful to separate the different types of leukocytes from each other, as a tool in typing of leukemias and lymphomas (See e.g., U.S. Pat. No. 5,234,816), and to obtain blood stem cell progenitor fractions isolated away from other cell types (U.S. Pat. No. 5,137,809, Aug. 11, 1992), for research and for therapeutic uses. Flow cytometers have become routine in clinical laboratory use. Several parameters of a cell may be measured simultaneously: forward scattered light is used to measure cell size; and a second scatter detector provides information on the granularity of the cell cytoplasm. These methods can be used to differentiate the various types of leukocytes. Fluorescent light emitted from various "fluorochromes," each of which is bound to a specific cellular target molecule, is collected by the cytometer. These parameters create a broad range of applications dependent on the specificity and combination of a dye-conjugated molecule and its target.

Although cytometry today relies upon correlated analysis of 3-4 color data, the field is rapidly moving toward use of more probes/cell to dissect complex inter and intracellular events by analyzing the characteristics of various subpopulations of cells in complex mixtures (as, e.g., in a developing immune response). The nature of excitation and emission characteristics of fluorochromes makes it difficult to select more than three or four visible emitting fluorochromes attachable to cells which provide emissions sufficiently separated in wavelength to give good spatial and/or spectral discrimination.

General labeling of cell proteins or membranes with stable fluorescent probes is also a powerful method for delineating intricate cell-cell interactions, as for example when analyzing immune system functions. However, currently available protein and membrane labels, such as CFSE (Molecular Probes)

and the PKH dyes (Sigma), have significant limitations when studying cellular interactions and responses both in vivo and in vitro. Because they excite and fluoresce in the visible regions of the spectrum, high levels of tissue scattering and autofluorescence can render such dyes unsuitable for optical imaging in intact animals. In addition, cellular autofluorescence limits the signal:noise (S/N) ratio that can be achieved and significant spectral overlap with other commonly used visible fluors complicates instrument setup when such dyes are used for flow cytometry or confocal microscopy. Although longer wavelength analogs of DiO and DiI that are applicable to general membrane staining are known in the art, time as well as concentration must be varied to achieve optimum staining with these dyes.

The complex cell types, trafficking and localization patterns, signaling mechanisms, and regulatory feedback loops which constitute the innate immune system allow it to respond highly selectively to a particular antigen or pathogen and also offer the potential to selectively enhance or interfere with a response. However, this selectivity is achieved primarily based on localized encounters involving antigen, antigen presenting cells, and lymphocytes in the context of tissue specific adhesion molecules and secreted molecular messengers such as chemokines and cytokines. Therefore, productive intervention in the immune surveillance and response process requires the ability to dissect and monitor complex cellular interactions in vitro, ex vivo, and in vivo. The ability to selectively tag different cell types and follow their fate is critical to understanding immune responses in sufficient detail to design and optimize effective treatment strategies involving immunotherapy.

General membrane labeling with fluorescent lipophilic dyes which intercalate stably into cell membranes is simple, rapid, and applicable to almost any cell type. Currently available probes of this type have been utilized for purposes of tracking and identifying specific cell types and they offer several advantages in contrast to utilizing general protein labeling for such purposes. Since labeling is non-covalent and occurs by partitioning into the lipid bilayer, there is no waiting period for fluorescent intensity to stabilize, such as is required for covalent protein labels (e,g., CFSE), and untoward effects on cellular receptor-ligand interactions and associated responses are typically minimal.

The most common fluorophores used to label cells and biomolecules were originally developed for microscopy, and for reasons of compatibility with available light sources and the human eye, fluoresce primarily in the UV and visible regions of the spectrum (approximately 400 to 600 nm). Dilution of membrane intercalating dyes among daughter cells has proven very useful for monitoring differential cell proliferation responses in complex populations and for tracking of cells in responding to stimuli such as antigenic challenge. Like general protein labels, concentration of membrane dyes is halved with each cell division, thus limiting use for long term tracking. Also, in both general protein labeling and fluorescent membrane labeling, high labeling intensity (often 1-2 orders of magnitude greater than bright antibody labeling) can complicate filter selection and color compensation when used in combination with other probes.

The above challenges and limitations to fluorescent labeling have brought increasing interest in development of fluors that excite and emit in the FR (far red) and NIR (near infrared) wavelengths. Although usage in the literature varies considerably, we here define FR as about 600-700 nm and NIR as about 700-900 nm, since water absorption and thermal background begin to interfere with measurement of biological fluorescence at >900-1000 nm. The use of FR or NIR fluors has a number of significant advantages in biological systems in general, and for cellular analysis in particular. These include i) decreased background caused by tissue or protein autofluorescence, ii) decreased background caused by Raman scatter, iii) less spectral overlap when used in conjunction with common UV or visible fluors, and iv) excitation and emission profiles compatible with the use of inexpensive excitation sources (e.g. diode lasers) and detectors (e.g. avalanche diodes). FR fluorescing analogs can be used on existing flow cytometers and confocal microscopes, since many of these instruments have FR excitation capability (HeNe, 635 nm diode, or 647 nm Kr/Ar lasers). Use of FR analogs therefore provides i) ability to do longer term in vitro and in vivo tracking of dividing cells due to reduced background and improved signal/noise ratio and ii) simpler instrument setup due to reduced spectral overlap.

Utilization of NIR fluorescence has significant advantages over even FR imaging for in vivo optical imaging of intact tissues or animals. In addition to decreased background from autofluorescence and Raman scattering, NIR light is better transmitted in vivo and thus real time fluorescence imaging can be performed through millimeters to centimeters of tissue. In fact, the longer the wavelength of the exciting light or the NIR flourescence, the better the tissue penetration, due to reduced elastic scattering and the fact that the few biomolecules which absorb in this region (hemoglobin and deoxyhemoglobin) do so only weakly. FR and NIR labeled antibodies or polymers have been shown to enhance contrast between normal tissue and tumors. Current depth of detection is in the 0.5-1 cm range but NR light can travel through tissue for 5-6 cm.

It is known that adjusting the composition of aromatic groups and the number of methine groups separating the aromatic groups of cyanine dyes causes changes in the light excitation and emission patterns and color of these dyes. In general, increasing the number of methine groups separating aromatic components of the dyes will shift the emission spectra toward the red and near infrared wavelengths. Increasing the length of the methine bridge between aromatic groups, however, also increases the overall liphophilicity of the compound and thus will reduce the solubility of such compounds, limiting their utility as membrane probes. This limitation can be overcome if appropriate compositions for labeling are selected which afford sufficient aqueous solubility to be compatible with sensitive biological materials (e.g., cells) while minimizing the negative impact of standard physiological media and salts on the lipophilic substances.

SUMMARY OF THE INVENTION

Accordingly, the present invention is directed to novel membrane intercalating dyes (also referred to herein as "probes") that fluoresce in the far red and near infrared segments of the spectrum and are soluble in commercially available membrane staining diluents. These probes are useful in diagnostic and therapeutic applications. The present invention is also directed to compositions containing the probes in pharmaceutically acceptable aqueous and non-aqueous labeling vehicles suitable for staining biological materials.

In another aspect, the invention provides methods of contacting the probes with cells and/or other lipophilic structures, allowing the probes to intercalate with the lipophilic structures, and detecting the cells or other lipophilic structures in vitro and or in vivo based on the fluorescence emitted therefrom.

In a preferred embodiment, the invention is directed to method of labeling epithelial cells in vivo with cyanine dyes to provide an in vivo method for diagnosing disease states which are characterized by the presence of abnormal cell shedding rates amongst mature epithelial cells.

To achieve these and other objects, the present invention provides an in vivo method for detecting abnormal cell shedding rates amongst mature epithelial cells, such as epithelial cells of mucosal surfaces, of a warm-blooded animal comprising the steps of labelling mature surface epithelial cells at a target site with FR and NIR probes and thereafter monitoring the site for the presence or absence of the label. In a preferred embodiment of this method, the cells which are labeled reside on mucosal surfaces; amongst which mucosal surfaces of the gastrointestinal tract provide particularly preferred targets. The present invention also provides a method for diagnosing disease states characterized by abnormal cell shedding rates amongst mature epithelial cells of a warm-blooded animal, comprising labeling mature epithelial cells with the FR and NIR probes of the invention, determining the shedding rate of the labeled-cells and comparing the shedding rate of the labeled cells to the known shedding rate of similarly located healthy epithelial cells.

DESCRIPTION OF THE PREFERRED EMBODIMENTS

Reference will now be made in detail to the presently preferred embodiments of the invention. The invention provides compounds that are novel membrane intercalating dyes (also referred to herein as "probes") that fluoresce in the far red and near infrared segments of the spectrum and methods for their use. The invention also provides labeling compositions comprising the probes solubilized in a labeling vehicle. The probes are solubilized in a vehicle compatible with the biological and/or solvent sensitivities of the materials to be labeled.

The compounds contain lipophilic tails (referred to herein in the structures as "R" and "R'") that in some embodiments are equal in length while in some preferred embodiments, R≠R'.

It is contemplated that the probes of the present invention may be used in conjunction with other labeling techniques and reagents for multiparameter cell tracking and sorting procedures. Usefulness of a dye in combination with others is traditionally determined by two aspects of spectra of light energy interactions: (1) the extent to which a dye molecule is excited by a single illumination wavelength or narrow band of wavelengths and (2) the extent to which each excited dye molecule emits light of wavelength sufficiently different from the other dyes so as to be discernible as a unique color or peak. The first aspect enables the user to illuminate the multiply-stained biological sample with a single wavelength and the second aspect enables the user to observe and record different colors of emission, each of which is associated with a particular cell type or a structure.

There are a number of new detectors under development in which the entire spectrum of light is collected and then the curves characteristic of each probe's emission are devolved from the aggregate signal taken over the entire spectrum. It is also contemplated that the probes of the present invention will be readily detected using such instruments.

The probes of the invention, when used as membrane-intercalating dyes selectively stain cell membranes in vitro, ex vivo and in vivo and do not undesirably affect the nature of the cells. The probes and thus the cells or other lipophilic structures to which they become attached can be readily identified by the fluorescence they emit. In addition, the compounds of the present invention are not cytotoxic when used at appropriate concentrations, are stably retained in cell membranes, and stain cells rapidly. The probes need only be applied to cells for a few minutes to achieve staining intensities 100-1000 times greater than background autofluorescence. Another beneficial-aspect of the compounds of the present invention is that they are soluble in isotonic salt free diluents suitable for membrane labeling such as Diluent C (Sigma-Aldrich Corporation). The probes of the present invention are useful generally as agents for cell labeling, cell sorting and cell tracking in vitro and in vivo for both basic (laboratory) and clinical research. For examples of such uses, see U.S. Pat. Nos. 5,385,822; 5,256,532, the disclosures of which are incorporated by reference herein; and U.S. Pat. Nos. 4,859,584; 4,783,401 and 4,762,701. Such probes will be useful, for example, as research reagents for use in existing flow cytometers and confocal imaging systems which have FR and/or NIR capabilities.

The probes of the present invention will 1) bind to cells in sufficient number to give a good signal compared to autofluorescence; 2) not be toxic to the cells at that level, and 3) be retained in the cell membrane long enough for tracking and/or sorting of particular subgroups of cells to be completed.

The invention provides probes that exhibit<5% change in HPLC purity for at least 2 months in solid form when stored at room temperature and at least 1 month in ethanol and maintain>60% of their initial solubility in an ethanol control for at least 30 minutes in an aqueous vehicle.

The FR/NIR probes of the invention exhibit<10% photobleaching after 24 hr under ambient lighting typical to indoor fluorescent lighting.

The FR probes of the invention result in<10% reduction in cell viability and<10% alteration in the population doubling time of cultured YAC lymphoma cells after labeling with concentrations sufficient to give starting S/N ratios>100.

The NM probes of the invention result in<10% reduction in cell viability and<10% alteration in the population doubling time of cultured YAC lymphoma cells after labeling with concentrations sufficient to give starting S/N ratios>10.

The FR probes of the invention are retained in cellular membranes well enough to maintain an S/N>100 after 24 hrs co-culture with unlabeled cells even when culturing is carried out under conditions where dye intensity is decreased by cell growth.

The NIR probes of the invention are retained in cellular membranes well enough to maintain an S/N>10 after 24 hrs co-culture with unlabeled cells under conditions where dye intensity is decreased by cell growth.

The FR and NIR probes of the invention require<40% correction for spectral overlap in the phycoerythrin channel, as evaluated by flow cytometry.

The lipophilic nature of the probes of the present invention provides for the efficient incorporation of the probes into various lipid containing or hydrophobic structures, including cell and viral membranes, liposomes, microspheres and the like. When incorporating the probes into cells and virions, a labeling composition comprising the probe and an aqueous labeling vehicle is mixed with the target to be labeled. The labeling composition contains a cyanine dye in a vehicle (diluent) that is safe for application and that provides reproducible cell labeling. Osmolarity regulating agents in which cyanine dyes form stable solutions for at least as long as required for labeling can be used. Acceptable osmolarity regulating agents may be selected from sugars including monosaccharides such as glucose, fructose, sorbose, xylose, ribose, and disaccharides such as sucrose; sugar-alcohols including mannitol, glycerol, inositol, xylitol, and adonitol; amino acids including glycine and arginine; and certain Good's buffers such as N-tris(hydroxymethyl)-methyl-3-aminopropanesulfonic acid. Small amounts of buffering agents may be added to the labeling medium to regulate hydrogen ion concentration (pH) to physiological and/or non-toxic levels. Other conventional agents, such as antibiotics and preservatives, may be also be employed in the vehicle, but only to the extent that they do not create salt concentrations that induce rapid formation of dye micelles or aggregates.

When incorporating the probes into microspheres or liposomes and like materials which can tolerate exposure to non-aqueous labeling vehicles without detrimental effect, a labeling composition comprising the probe and a non aqueous labeling vehicle is mixed with the target to be labeled. Non aqueous labeling vehicles include polar organic solvents such as ethanol, dimethyl formamide, dimethylsulfoxide, and the like.

Despite their lipophilic nature, we have found that the probes of the present invention are sufficiently soluble in aqueous vehicles to allow efficient and rapid staining of lipophilic structures (membranes and the like) which are detrimentally affected by exposure to polar organic solvents.

The detection step can employ a luminescence microscope or other optical imaging apparatus such as e.g., a fiber optic diagnostic device such as a cystoscope or endoscope and the like, having a filter for absorption of scattered light of the excitation wavelength and for passing the wavelength that corresponds to the fluorescence corresponding to the particular dye label used with the specimen. Preferred methods of observation and analysis include direct visualization with a microscope fitted with a light source and filters appropriate to the excitation and emission wavelengths, and use of a camera attached to the microscopes.

A preferred method of the invention for cell separation and enumeration of live cells appropriately stained with this class of probe reagents, is isolation by use of flow cytometry apparatus such as by way of examples only a FACSCalibur instrument with sorting capability or a FACSVantage instrument with cell sorting capability. Other similar instruments are well known in the art. These instruments illuminate a mixed cell population, for example at a given wavelength with an argon laser source of light, and use an emission signal from each cell detected in a moving fluid such as a buffer, to sort each cell as it is flowing past the detector using a variety of filters for collection of emitted light using techniques well known in the art. The apparatus can count and/or collect cell populations based on calculations employing measures of emitted right yielding both data and cell fractions for further analysis and use.

Recent advances in technology have made it possible to do fluorescence imaging not only at the microscopic (cellular and subcellular) level but also at the macroscopic (whole tissue or whole body) level. The probes of the present invention provide useful solutions to the problem of spectral "pollution" or spill, which is frequently encountered when doing multiprobe studies using confocal imaging or other quantitative microscopy techniques. In addition, the NIR probes, when combined with macroscopic imaging methods, provide a useful alternative to radiolabels for monitoring immune cell trafficking, localization and redistribution in intact animals as well as potential for use in diagnosis and/or phototherapy.

In another preferred embodiment, the probes of the present invention are, a subject for detection of abnormal epithelial cell shedding rates in vivo such, as described in U.S. Pat. No. 5,804,389. In this process, the abnormal shedding of epithelial cells in a warm-blooded animal is determined. The process includes the steps of labeling mature surface epithelial cells with the compounds of the present invention at a target site, exposing the cells to light of an excitation wavelength and thereafter monitoring the site for the presence or absence of the label, and observing the loss of detectable label over a pre-defined period of time. The present invention also provides a method for diagnosing disease states characterized by such abnormal cell shedding rates amongst mature epithelial cells of a warm-blooded animal, comprising labeling mature epithelial cells, determining the shedding rate of the labeled cells and comparing the shedding rate of the labeled cells to the known shedding rate of similarly located healthy epithelial cells.

The probes of the present invention can be utilized to determine abnormal shedding rates on any epithelial surface of the body. Surfaces include those of the stomach, biliary tract, colon, urinary tract-blood vessels, pulmonary tract-including the nasal cavity, cornea, esophagus, pancreatic duct, small intestine, and genital organs including the vagina and ovarian duct and the prostate gland. Preferably, the composition in solution form is administered by direct application (e.g. spraying) onto the surface of the epithelial mucosa under direct vision by endoscope, by flooding the surface with a solution, or by orally administering the solution to the subject in the form of a drink.

When in vivo use in humans is contemplated, a solution of any of the compounds of the present invention can be prepared by dissolving an effective amount of the probe in an isoosmotic, aqueous and preferably salt-free solvent miscible with both water and polar organic solvents. The concentration levels of dyes in compositions for in vivo use according to the present invention will be similar to or greater than the concentration levels used in the previously-known in vitro cell staining applications of those dyes. The precise concentration to be administered can be varied and can be readily optimized. The volume of probe composition to be administered will vary depending upon the concentration of the cyanine dye in the composition and upon the size of the target site. The administration volume may vary, for example, from about 1 to 100 ml and can be readily optimized. An administration volume of about 10 nil of the probe composition can be used in many applications. Administration route will vary depending upon the type of cells to be labeled. As indicated above, for staining of epithelial cells may be best achieved by oral administration or direct application. Other modes of administration, such as subcutaneous, intramuscular and intravenous injection and the like are also contemplated.

According to the preferred method of the invention, the cyanine dye label is detected by exposing the site of labeled cells to excitation light and observing and/or measuring the intensity of the fluorescence. For example, compound 8 (discussed infra in the examples) responds to excitation light of about 635 nm for the observation of maximum fluorescence at 667 nm, whereas compound 13 (also discussed infra in the examples) responds to excitation light of about 647 nm for the observation of maximum fluorescence at 713 mm.

The probes of this invention can be synthesized, as set forth in detail in the examples below.

The FR probes of the present invention can be detected by commercial cytometry instrumentation with the ability to excite fluors which absorb in the 600-700 mm range and emit in the 700-800 range (e.g., BD FACSVantage, FACSCalibur, Beckman Coulter Altra, and Cytomation MoFlo flow cytometer/sorters, and BioRad 1024ES or 1024MP confocal imaging systems). The advent of small benchtop cytometers (e.g. volume capillary cytometer in development by Biometric Imaging/BD which incorporate inexpensive diode lasers and diode detection systems will provide additional detection systems to quantify NIR fluorescence.

This near infrared/far red wavelength also is advantageous in that the background fluorescence in this region normally is low in biological systems and high sensitivity can be achieved.

A preferred labeling composition of the present invention comprises a cyanine dye of the formula:

[A-CR$_1$=CR$_2$—Y=CR$_3$—CR$_4$=B]$_Z$$^+$ wherein "—Y="

is selected from the group consisting of

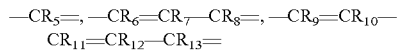

, and

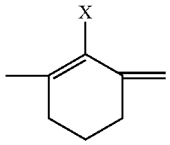

wherein each of R$_1$, R$_2$, R$_3$, R$_4$, R$_5$, R$_6$, R$_7$, R$_8$, R$_9$, R$_{10}$, R$_{11}$, R$_{12}$, and R$_{13}$ is independently H, halogen or an alkyl group having 1-4 carbons;

X is selected from the group consisting of H, halogen, O-alkyl, O-aryl, S-alkyl and S-aryl;

Z is a biologically compatible counterion;

"A-"

is a structure selected from the group consisting of

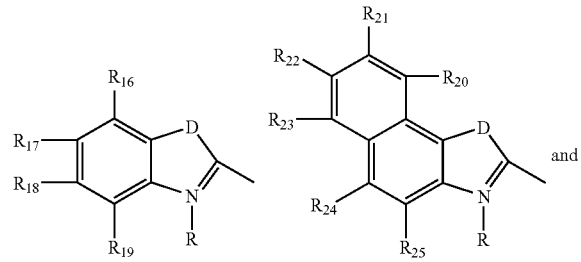

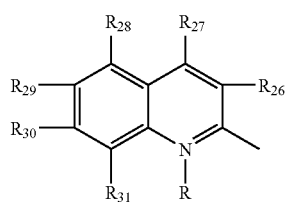

and "=B"

is selected from the group consisting of

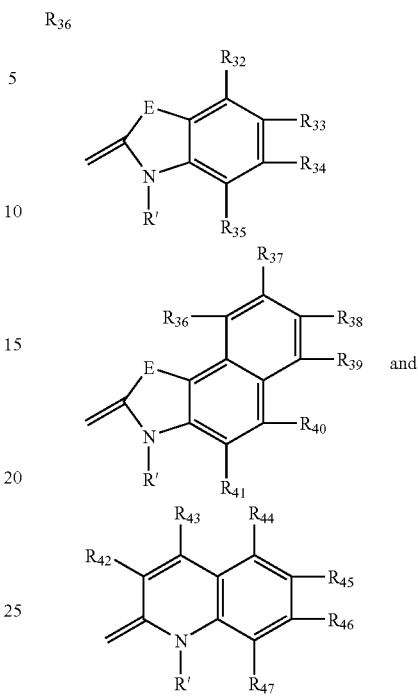

wherein D and E are each independently O, S or CR$_{14}$ R$_{15}$, where R$_{14}$ and R$_{15}$, which may be the same or different, are independently alkyl groups having 1-6 carbons. Alternatively, R$_{14}$ R$_{15}$ taker in combination complete a 5- or 6-membered saturated ring. Preferably X equals Y (yielding a symmetrical cyanine). In some preferred embodiments, both D and E are CR$_{14}$ R$_{15}$, where CR$_{14}$ R$_{15}$ are methyl or ethyl, more typically methyl.

Each of R$_{16}$-R$_{47}$ is independently H, halogen or an alkyl group of 1-4 carbons.

R and R' are each independently linear or branched hydrocarbons having 7-30 carbons, with the proviso that one of R and R' must be at least 14 carbons.

Z is a biologically compatible counterion that is typically an anion that balances the intrinsic positive charge of the cyanine dye and is present in such a number and with such a total charge as to make the overall molecule electrically neutral. As used herein, a substance that is biologically compatible is not toxic as used, and does not have a substantially deleterious effect on biomolecules. Such compounds also must not undesirably affect cell viability in the concentrations required for labeling. Accordingly, pharmaceutically acceptable forms of the cyanine dye other than the iodide salt may be employed in some instances, including other pharmaceutically acceptable salts. Examples of useful counterions for dyes having a net positive charge include, but are not limited to, chloride, bromide, iodide, sulfate, alkanesulfonate, arylsulfonate, phosphate, perchlorate, tetrafluoroborate, nitrate and anions of aromatic or aliphatic carboxylic acids. Selection of an appropriate anion, however will be limited by the particular anions' affect on solubility, since it is known that the anion associated with the various lipophilic molecules can effect the solubility of the compound.

In a preferred embodiment, the counter ion is iodide. In certain instances, such as for in vivo administration of the probes, it may be preferable to substitute the iodide counterion with a chloride, since some individuals are allergic to iodine.

The present invention is further described in the following examples which are provided for illustrative purposes only and are not to be construed as limiting. Standard techniques well known in the art or the techniques specifically described below are utilized.

EXAMPLE 1

Synthesis of Probe with 667 nm Emission (8)

A membrane-probe with 667 nm Emission was prepared according to the following synthetic reaction Scheme 1.

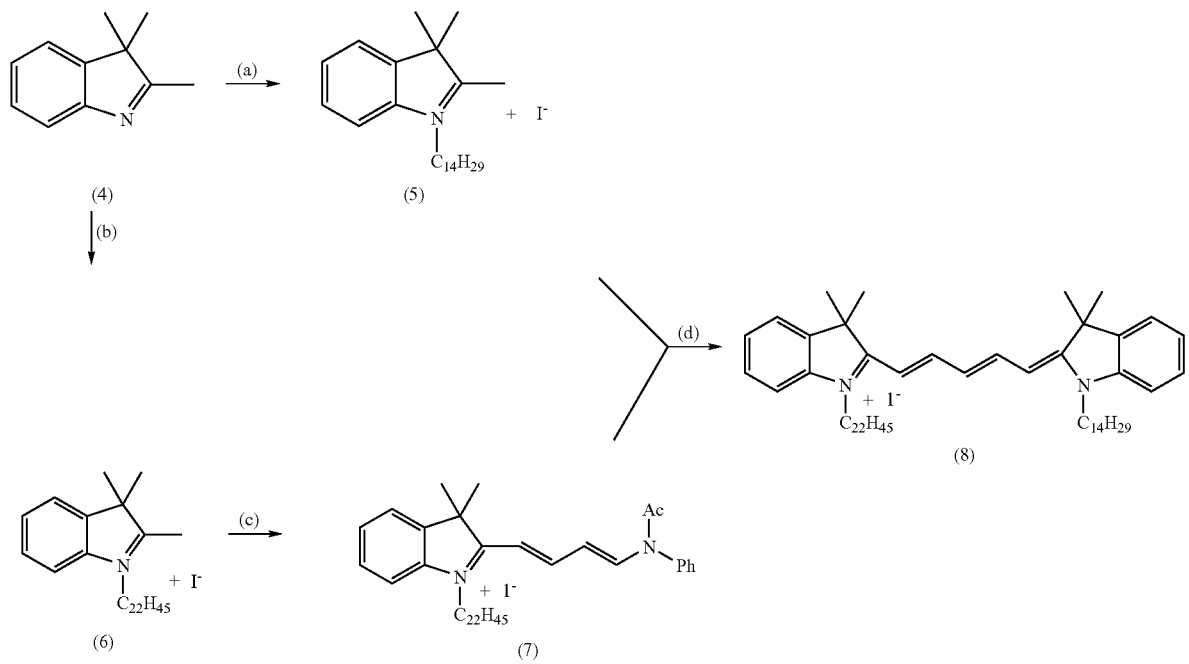

Preparation of 1-tetradecyl-2,3,3-trimethylindolinium Iodide (compound 5)

Tetradecyl-1-(4-chlorobenzenesulfonate): To a stirred solution of tetradecanol (26.3 g, 0.123 mol, Aldrich Chemical Co., Milwaukee, Wis.) and 4-chlorobenzenesulphonyl chloride (28.48 g, 0.123 mol, Aldrich) in dichloromethane (500 ml) at room temperature is added triethylamine (28 ml, Aldrich) in dichloromethane (200 ml) dropwise. The resulting solution is stirred for 48 hours. The reaction mixture is then washed with water (3×400 ml) and the dichloromethane layer dried over sodium sulfate and concenetrated. The crude solid obtained was recrystallized from methanol to provide pure tetradecyl-1-(4-chlorobenzenesulphonate)(29.9 g, 62%) as a white solid. 200 MHz proton NMR (CDCl$_3$): 0.88 (t, J=7.0 Hz, 3H), 1.10-1.80 (m, 24H), 4.05 (t, J=7.0 Hz, 2H), 7.50-7.60 (m, 2H), 7.80-7.90 (m, 2H).

2,3,3-trimethyl-(3H)-indoleine (4) (6.36 g, 0.04 mol, Aldrich) and tetradecyl-1-(4-chlorobenzenesulfonate) (15.52 g, 0.04 mol) are heated together with stirring at 130-140° C. for 3 h. The reaction mixture is then cooled to room temperature and dissolved in ethanol (200 ml). A saturated solution of potassium iodide (200 ml) is added and this mixture is stirred for 30 minutes 1.5 L of distilled water is then added and after a further 15 minutes stirring, the solid precipitate is collected, washed with water and dried under vacuum. The crude material is recrystallized from ethyl acetate to provide pure intermediate compound 5 (11.9 g, 62%). 300 MHz proton NMR (CDCl$_3$): 0.88 (t, J=7 Hz, 3H), 1.25-1.50 (m), 1.67 (s, 6H), 1.93 (m, 21), 3.13 (s, 3H), 4.70 (t, J=7.70 Hz, 2H), 7.60-7.66 (m, 4H).

Preparation of 1-docosanyl-2,3,3-trimethylindolinium Iodide (6)

Docosanyl-1-(4-chlorobenzenesulfonate): To a stirred solution of docosanol (47.8 g, 0.15 mol) and 4-chlorobenzenesulphonyl chloride (34.01 g, 0.16 ml, Aldrich) in dichloromethane (500 ml) at room temperature is added triethylamine (33.5 ml, Aldrich) in dichloromethane (200 ml) dropwise. The resulting solution is stirred for 48 h. The reaction mixture is then washed with water (3×400 ml), the organic layer dried over sodium sulfate and concentrated to~400 ml to initiate crystallization of the product. After cooling and aging the precipitate is collected by filtration and dried under vacuum to provide pure docosanyl-1-(4-chlorobenzenesulphonate) (48.9 g, 73%) as a white solid. 300 MHz proton nmr (CDCl$_3$): 0.88 (t, J=7.0 Hz, 3H), 1.15-1.40 (m), 1.55-1.75 (m, 2H), 4.02 (t, J=7.0 Hz, 2H), 7.48-7.60 (m, 2H), 7.78-7.90 (m, 2H).

2,3,3-trimethyl-(3H) indoleine (6.3 g, 0.04 mol, Aldrich) and docosanyl-1-(4-chicrobenzenesulfonate) (20.0 g, 0.04 mol) are heated together with stirring at 130-140° C. for 3 h.

The reaction mixture is then cooled to room temperature and the waxy solid dissolved in ethanol (250 ml). A saturated solution of potassium iodide (200 ml) is, added and this mixture stirred for 30 minutes 1.0 L of distilled water is then added and after a further 15 minutes stirring, the solid precipitate is collected, washed with water and dried under vacuum. The crude material is recrystallized from dichloromethane/hexane to provide pure intermediate compound 6 (14.5 g, 61%). 200 MHz proton NMR (CDCl$_3$): 0.87 (t, J=7.0 Hz, 3H), 1.15-1.50 (m), 1.67 (s, 6H), 1.85-2.00 (m, 2H), 3.10 (s, 3H), 4.70 (t, J=7.7 Hz, 2H), 7.55-7.70 (m, 4H).

Preparation of 1-docosanyl-2-[(4-N-phenyl-N-acetylamino)-1,3-butadienyl]-3,3-dimethylindolinilim iodide (7)

A solution of (6) (2.38 g, 4-mmol) and malonaldehyde bisphenylimine hydrochloride (1.10 g, 4.4 mmol, TCI America, Portland, Oreg.) in acetic anhydride (30 ml) is heated at 100-110° C. for 1 h, cooled to room temperature and filtered. The filtrate is then diluted with 300 ml of water and placed in a refrigerator at 0-5° C. for 24 h. The resulting precipitate is collected and dried under vacuum to provide (7) (0.65 g, 21%). 300M proton NMR (CDCl$_3$): 0.88 (t, J=6.5 Hz, 3H), 1.20-1.40 (m), 1.70 (m), 1.80 (s, 6H), 2.24 (s, 3H), 4.36 (t, J=7.5 Hz, 2H), 5.79 (t, J=12.8 Hz, 1H), 6.71 (d, J=15.0 Hz, 1H), 7.25-7.70 (m, 9H).

A probe with this emission wavelength was selected for synthesis because it is red shifted by>100 nm compared with most other visible fluorescent probes used for cell labeling and therefore has minimum spectral overlap with them. This probe could therefore be ideal for use in flow cytometry and confocal microscopy when multiprobe labeling is required.

EXAMPLE 2

Synthesis of FR Probe with 713 nm Emission (13)

This compound prepared from compound 9 (available from Fisher/Acros Chemicals) as shown in Scheme 2 below using similar types of reactions and conditions to those described for compound (8).

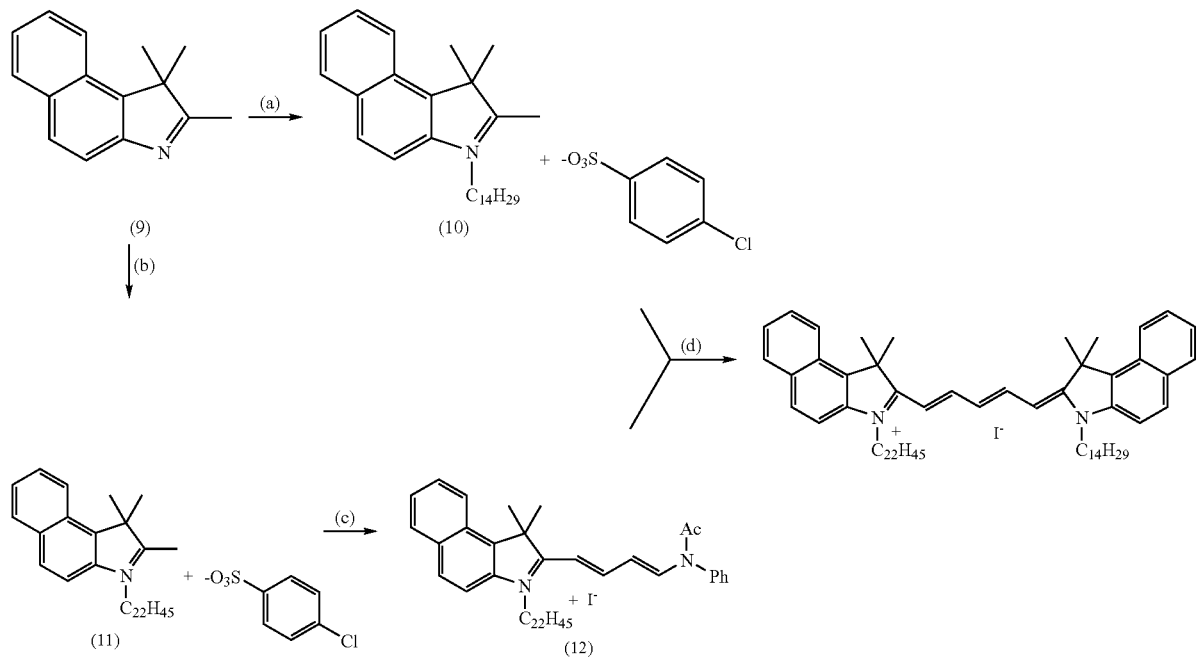

Intermediate compound 7 (0.544 g, 0.71 mmol) and intermediate 5 (0.343 g, 0.71 mmol) are heated together in refluxing dichloromethane (10 ml) containing 10 drops of triethylamine for 3 h. The reaction is monitored by TLC (5% methanol in dichloromethane). The reaction mixture is then concentrated by rotary evaporation and the residue crystallized from methanol at −20° C. overnight. The solid is collected and purified further by silica gel flash column chromatography eluting with 5-7.5% methanol in dichloromethane. Pure fractions are combined and concentrated to provide compound 8 (210 mgs, 30%). Purity>97% by HPLC. 300 MHz proton NMR (CDCl$_3$): 0.88 (t, J=6.3 Hz, 6H), 1.25-1.55 (m), 1.66 (m), 1.81 (s, 16H), 4.04 (t, J=7.4 Hz, 4H), 6.29 (d, J=13.6 Hz, 2H), 6.78 (t, J=12.4 Hz, 1H), 7.05 (d, J=7.8 Hz, 1 Hh.), 7.20-7.70 (m, 2H), 7.33-7.38 (m, 4H), 8.32 (t, J=13.0 Hz, 2H). Electrospray mass spectroscopy. M'=860. UV/VIS (ethanol): λmax=648 nm, c=189,270M-1 cm-1. Fluorescence (ethanol): excitation max.=647 nm, emission max.=667 nm.

EXAMPLE 3

Synthesis of FR Probe with 682 nm Emission (25)

This compound was synthesized by coupling of intermediate 6 from reaction scheme 1 with intermediate 10 of reaction scheme 2 under standard conditions. The compound was purified by column chromatography using standard conditions. This compound provides a far red emitting probe with absorbance and fluorescence properties intermediate to compound (8) and compound 13. The final isolated yield for this product was slightly lower (11.5%) than for Compound (8) and compound (13) due to difficulty in removing the symmetrical byproduct formed by dimerization of intermediate 7.

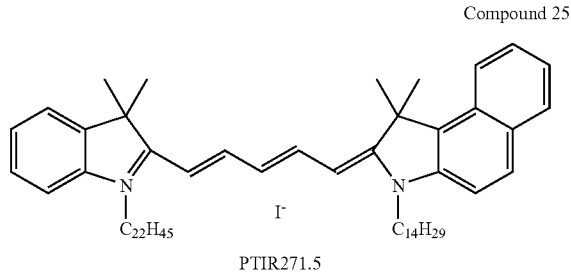

Compound 25

PTIR271.5

EXAMPLE 4

Synthesis of NIR Probe with 814 nm Emission (15)

This compound is prepared as shown in Scheme 3 below, using similar types of reactions and conditions to those already described above. The desired probe is purified by recrystallization or chromatography.

EXAMPLE 5a

Synthesis of NIR Probes with 837 nm Emission (19) and (26)

Compound 19 is prepared as shown in Scheme 4a.

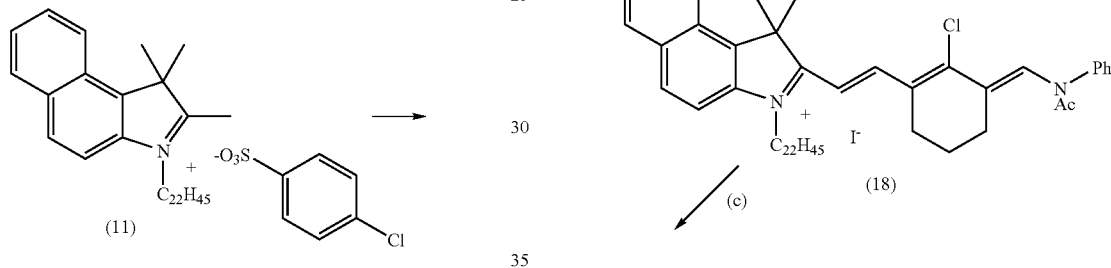

Compound 17 is prepared in ~27% yield according to procedures known in the art. Heating compound (11) with Compound 17 furnishes intermediate compound 18 in good yield. Reaction of Compound 18 with Compound 10 under the standard base coupling conditions will provide Compound 19. This probe is closely matched with commercially available diode lasers with emission wavelength of 810 mm. Excitation at wavelengths above 800 mm are to be used when labeling structures that are observed at relatively greater tissue depths, due to reduced light absorption by hemoglobin and myoglobin at these wavelengths, while maintaining the advantages of decreased scattering and autofluorescence associated with NIR illumination in general. As with compound 15, cells labeled with compound 26 should be readily detected using techniques well known in the art.

Scheme 4b-

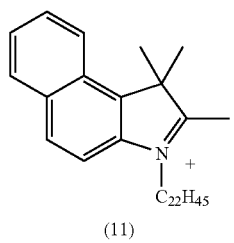

Compound 26

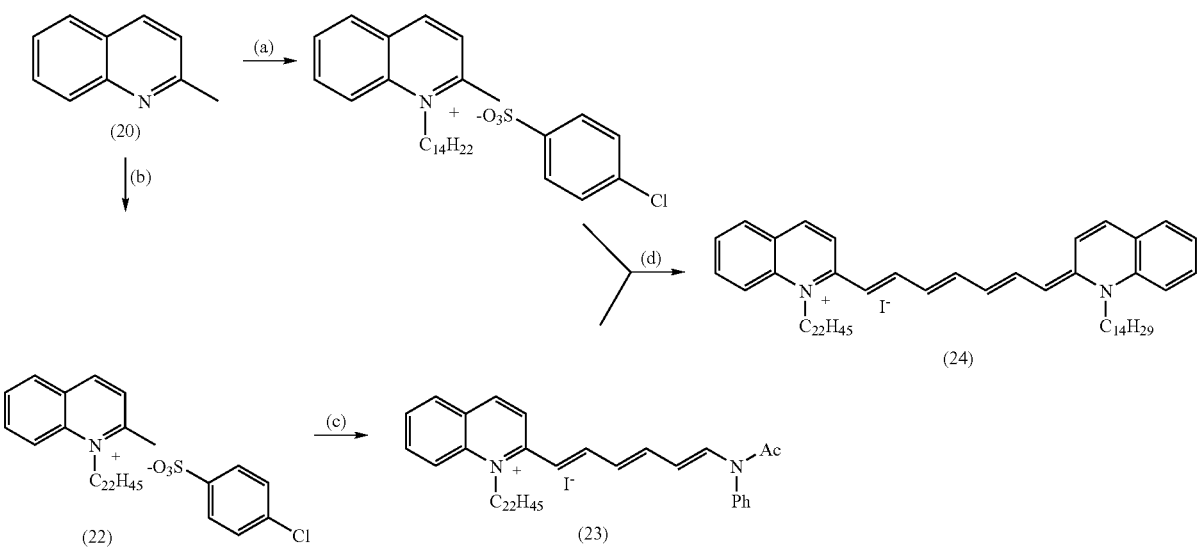

EXAMPLE 6

Synthesis of a NIR Probe with 900 nm Emission (24)

Excitation and emission further into the IR can be desirable to increase tissue penetration and depth of strutures detectable using macrosopic imaging. This compound is prepared as shown in Scheme 5, using reactions similar to those described above.

-continued

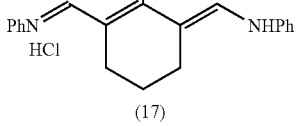

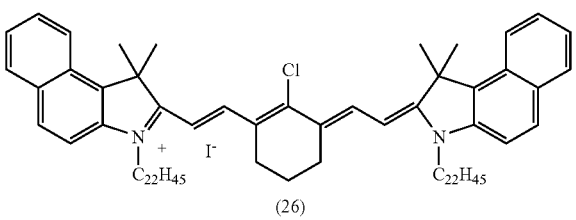

The optimal conditions for coupling of 17 with 2 mole equivalents of 11 is reflux in ethanol containing sodium acetate. The resulting compound is treated with potassium iodide and purified by silica gel chromatography.

EXAMPLE 7

Absorbance/Emission Spectra

Referring now to Table 1 there are shown representations of the absorbance and emission properties of some example compounds of the present invention. Absorption and Fluorescence spectra were nm using 0.25 μM solutions in ethanol on a Jasco, Inc. UV-530 UV/VIS spectrophotometer and FP 750 spectrofluorometer, respectively. Approximate extinction coefficients were estimated from the absorbance scans by dividing the maximum absorbance by the nominal concentration (25 μM).

TABLE 1

| Compound | Absorbance Max | Excitation Max | Emission Max |
|---|---|---|---|
| 8 | 626 | 647 | 667 |
| 13 | 684 | 680 | 713 |
| 15 | 786 | 790 | 814 |
| 25 | 666 | 667 | 682 |
| 26 | 824 | 824 | 837 |

EXAMPLE 8

Chemical Stability of FR/NIR Probes

Chemical stability of example compounds of the present invention when stored at room temperature as a solid or as a 1 mM solution in ethanol was determined by HPLC. Integration of the peaks detected for example compounds of the present invention at 260 nm was used to estimate chemical stability. All compounds tested displayed<5% change in HPLC purity when held as a solid at room temperature for two months and when held as a 1 mM liquid solution in absolute ethanol at room temperature for one month.

EXAMPLE 9

Photostability of FR/NIR Probes 1 mM solutions of the indicated probes in absolute ethanol were placed under normal fluorescent room lighting. Aliquots were taken from each sample shortly after preparation and the absorbance measured at the absorbance maximum for each probe as in Example 6. The absorbance of each sample was again measured after 24 hours at room temperature under ambient fluorescent light. All probes were stable, exhibiting<5% photobleaching for each compound.

EXAMPLE 10

Solubility of FR/NIR Probes

Effects of the various combinations of asymmetrical and symmetrical alkyl chains and methene bridges on the solubility of the compounds of the present invention were examined. Compounds 8, 25, 13, 15 and 26 were all soluble in ethanol at concentrations≧1 mM. The more lipophilic probes 15 and 26, however, required sonication for a few minutes to achieve dissolution at 1 mM in ethanol. All example probes-were poorly soluble in water. Triplicate 1:50 dilutions of stock 1 mM probe solutions were made in either ethanol or test diluent. After 30 minutes at room temperature solutions were centrifuged at 10,000×g for 10 minutes to remove any microaggregates and 100 ml aliquots were transferred to 2.0 ml of ethanol for absorbance determinations. Based on the teachings of Leung et al. and on solubility specifications found on Sigma Certificates of Analysis for the commercial diluents (diluent supernatant absorbance at 30 minutes at least 60% of ethanol supernatant absorbance after 30 minutes), a preliminary specification at least 60% of the ethanol control was set as a surrogate for solubility sufficient to achieve cell labeling with S/N ratios greater than 100 and to minimize potential problems with brightness or reproducibility of labeling. None of the probes was as soluble after 30 minutes in Diluent C as PKH26 (86%±4% of ethanol control). We have found, however, that at least for compound 8, 25 and 13, cells stained using compositions of dye in Diluent C gave S/N ratios substantially greater than those for PKH26 (Table 2), indicating that solubility was not a limiting factor for cell labeling. After 30 minutes, compounds 8 and 15 retained approximately 65% of their solubility at T0, compounds 13 and 25 greater than 55% of their solubility at T0, and compound 26 retained approximately 20% of its solubility in Diluent C at T0. This example demonstrates that the addition of polar groups or other substituents to enhance water solubility as taught by Leung et al. is not an essential prerequisite for bright and reproducible cell labeling with these-agents. In addition, it shows that useful levels of cell labeling can be obtained even when solubilities in iso-osmotic diluents are less than those taught by Horan et al.

EXAMPLE 11

Characterization of FR and NIR Probe Effects on Cell Viability, Cell Growth, and S/N Ratios YAC-1 murine lymphoma cells were stained at a concentrations of $10^7$ cells/ml with increasing concentrations of probe by rapidly admixing 2× cells suspended in Diluent C with 2× probe in Diluent C. After 5 minutes at room temperature, the staining was stopped by the addition of cell culture medium. Cells were then washed thoroughly (RPI1640+ 10.0% FBS) and cultured under standard conditions for 22-24 hours. Cell numbers were compared to those in a control culture treated with diluent alone.

Maximum Tolerated Concentration (MTC) of probe was defined as the highest concentration of probe at which (1) viability by trypan blue exclusion immediately post-staining was>90% and (2) YAC cell growth after 24 hours was no more than 10% different than growth of cells in diluent alone.

For S/N and spectral crossover determinations, cells were labeled in Diluent C using the MTC for each probe and then co-cultured with an equal number of unlabeled cells treated with diluent only. An aliquot of cells was fixed with 1% buffered methanol free formalin immediately after staining (T0) and analyzed on a flow cytometer. PMT high voltage on the flow cytometer was set so that the entire population of unlabeled cells lay in the first decade of the 4 decade log intensity scale, thereby allowing determination of a true mean value for unlabeled cells. When the intensity of stained cells was so great that the high voltage setting used for analysis caused a significant number of unlabeled cells to fall above the 4th decade, the high voltage setting was reduced to bring labeled cells fully on scale. Multilevel Rainbow beads from Spherotech (Libertyville, Ill.) were then run at both PMT settings and used to calculate adjusted intensity values for labeled cells based on the shift in intensity for the brightest bead peak. Results of viability are summarized in Table 2 below.

TABLE 2

| Compound | MTC | Cytotoxicity | Growth Inhibition | S/N at T = 0 | % Retention at T = 22 hours |
|---|---|---|---|---|---|
| Target Criteria | | <10% at T = 0 | <10% | >100 for FR >10 for NIR | >90% (growth-corrected) |
| PKH26 | 10 μM | <1% | <1% | 265 357 | 106% |
| compound 8 | 10 μM | <1% | <1% | 3948 | 98% |
| compound 25 | 10 μM | <1% | <4% | 1031 | 91% |
| compound 13 | 10 μM | <1% | <1% | 1152 | 90% |
| compound 15 | 10 μM | <1% | <5% | NC* | NC |
| compound 26 | 5 μM | <1% | <6% | NC | NC |

*denotes not compatible with excitation wavelengths and fluorescence detection filters available on unmodified commercially available instruments.

Fluorescence intensity data was accumulated in all-instrument channels without any compensation for spectral crossover. S/N was calculated as the ratio of the mean fluorescence intensity-per cell for labeled cells divided by the mean fluorescence intensity per cell for the in labeled diluent treated controls in the same co-culture. Percent retention was calculated as % of predicted MFI, where predicted MFI=MFI @T0/fold growth at T22-24 (to correct for growth related probe dilution). Percent spectral overlap (Table 3) was estimated as the ratio of MFI for labeled cells in the channel of interest to MFI in the primary channel for a given probe (channel with maximum S/N ratio).

TABLE 3

| | Compound | | |
|---|---|---|---|
| Channel | (8) FACS Calibur | (25) FACS Vantage SE | (13) FACS Vantage SE |
| FL2 488 nm excitation; 585/42 BP | 0.001% (MFI = 31) | ND | ND |
| FL3 Calibur: 488 nm excitation 661/16 BP Vantage 488 nm Excitation; 610/20 BP | 1.6% MFI = (−389) | 0 (MFI = 0) | 0 |
| FL4 Calibur: 635 nm excitation; 661/16 BP Vantage 647 nm excitation; 740 LP | NA* (MFI = 24430) | NA (MFI = 7180) | NA (MFI = 8087) |
| FL5 Vantage only: 647 excitation; 740 LP | NA | 62.4% (MFI = 4484) | 7.6% (MFI = 615) |

*denotes not applicable

EXAMPLE 12

Signal:Noise Estimation for In Vitro Imaging YAC-1 Tumor Cells Labeled with the FR/NIR Probes Logarithmically growing YAC-1 cells were labeled with PKH26 or example compounds of the present invention at the MTC for each probe. A Zeiss Axiophot inverted fluorescence microscope was used at 100× magnification in combination with a CCD camera and commercially available filter combinations to image labeled cells or unstained control cells. For these preliminary studies, acquisition times were chosen to achieve similar but sub-saturating signal intensities for all samples analyzed. Filter combinations used for data acquisition Although the off-the-shelf filters available from Chroma Technologies were not optimally matched with the excitation and emission spectra of the PTIR probes, good signal intensities were readily obtained for all of the new probes using relatively short acquisition times (5-500 msec.). Standard rhodamine filters (not shown) were used for PKH26 image acquisition, since these have a near optimal match to the excitation-emission characteristics of PKH26. Custom filter sets from Chroma, Technologies, Inc. were as follows: PKH26-standard rhodamine filter set;

compound 13—excitation HQ665/45, dichroic Q69OLP, emission HQ725/50;

compound 15—excitation HQ755/75, dichroic Q805LP, emission HQ860/100;

compound 26—excitation HQ775/50, dichroic Q805LP, emission HQ845/55.

Signal:Noise Estimates for Labeled Cells

Average fluorescence intensity was determined for each of 9 cell-associated analysis regions having an area of 44 arbitrary units (lightly shaded circles), avoiding measurements of pixels representing overlapping cells. Four additional non-cell-associated analysis regions, also with area of 44 arbitrary units (darkly shaded circles, N) were used to estimate noise level. Mean intensity of all cell associated regions was calculated (signal, S) as was the mean intensity of all non-cell associated analysis regions (noise, N). Mean noise values were similar for all 4 probes despite the wide range of imaging acquisition times employed, indicating that noise was being averaged over time. Since acquisition times varied widely (5 msec for COMPOUND 13, 50 msec for PKH26 and COMPOUND 15, 500 msec for COMPOUND 26), comparative estimates of S/N expected for a standardized 50 msec acquisition time were calculated as follows:

$$S/N(50\text{ msec})=S/N(\text{observed})\times @(50\text{ msec/actual acquisition time in msec}).$$

Despite the fact that spectral characteristics of probe and filters were significantly better matched for PKH26 than for the present probes, normalized SN increased as excitation emission characteristics shifted from visible (PKH26) to FR (compound 13) to NIR (compound 15). Without being bound by theory, the somewhat lower normalized SN observed for compound 26 may be due to a combination of lower staining concentration and lower efficiency of the excitation-emission filters.

Authfluorescence:Background Ratio for Unstained Controls

Because measurements at the longer wavelengths are not routinely performed and the filters used for the present probes were non-standard combinations, we also evaluated cell associated autofluorescence and non-cell associated background using the same filter windows used for analysis of labeled cell images. However, in this case a constant image acquisition time of 5000 msec (5 sec) was used for all-filter windows. Reduced autofluorescence signal was seen in the FR (compound 13) and NIR (compound 15 & 26) windows. In addition, background noise was reduced in the NIR (compound 15 & compound 26 filter windows) compared with the visible (PKH26) and FR (13).

EXAMPLE 13

Compatibility of Compound 8 and Compound 25 with Three Color Lymphocyte Subset Analysis on a BD FACSCalibur Benchtop Clinical Analyzer Human peripheral mononuclear cells (PBMC) were isolated from the blood of healthy individuals, labeled with compound 8 or compound 25 at concentrations similar to those used for proliferation monitoring with PKH26. A variety of monoclonal antibody reagents and fluorochromes useful for 3-color lymphocyte inimunophenotyping are known in the art. Several of these were evaluated for compatibility with use of the FR probes as the fourth color. After staining with compounds of the present invention, cells were additionally incubated with one of the fluorescent anti-PBMC antibody markers as indicated. Following antibody labeling, flow cytometric analysis was carried out using the BD FACSCalibur clinical analyzer as in Example 10. Post staining recovery was evaluated by comparing analysis time required to acquire 10,000 CD3+ lymphocytes and viability was assessed as % of lymphocytes able to exclude propidium iodide (PI).

Referring now to Table 4, there are shown the analyses of the effect of compound 8 and compound 25 labeling on three color lymphocyte subset analysis.

TABLE 4

| Mab-Fluorochrome | CD3-FITC | CD19-PE | CD8-cychrome | CD16-PE + CD56-PE | CD4-PerCP | CD8-cycbrome |
|---|---|---|---|---|---|---|
| Membrane probe | | | | | | |
| None | 73 | 3 | 3 | 20 | 49.8 | 27 |
| 1 µM Compound 8 | 73 | 2 | 3 | 21 | 49.4 | 27 |
| 2 µM COMPOUND 25 | 73 | 3 | 4 | 20 | 49.9 | 27 |

% of total lymphocytes positive for indicated monoclonal antibody; representative results from one of three experiments.

EXAMPLE 14

Visualization of FR Labeled Cells by Intact Organ Microscopy

MDA-MB-435s tumor cells were labeled with 5 µM compound 8 as in the above examples and infused intravenously into a rat. Isolated perfused intact lung preparations from infused rats were isolated and visualized using a BioRad Radiance 2000 confocal microscope. Photographic analysis of the superficial microvessels of an isolated perfused lung preparation enabled detection of areas labeled with compound 8 as red areas while green areas were indicative of cells labeled with CM-fluorescein protein label or autofluorescing endothelial cells. This example demonstrated the utility of tracking labeled cells in intact organ preparations.

EXAMPLE 15

In Vivo Tracking and Imaging of Tumor Cells Labeled with FR/NIR Probes

It is known in the prior art that NIR labeled antibodies can be attached to tumor cells and through visualition of the tumor cells with an image intensified video camera or a cooled CCD camera (46). YAC-1 cells were stained with PKH26, compound 8, compound 13, compound 15, and compound 26 at their respective MTC's (10 µM for all but compound 26 at 5 µM). This example demonstrated that bright fluorescence of cells labeled with compound 13, compound 15 and compound 26 can be detected through the skin of nude mice. $10^6$ YAC-1 cells in 20 µl volumes were injected subcutaneously into nude mice and the mice were anesthetized with Sodium Pentobarbital (30 Mg/kg) and set over a mobile stage. Excitation was performed with an optic fiber illuminator equipped with the appropriate excitation filter Emission was collected with the aid of a CCD camera equipped with a Nikon lens through the [KM1] emission filter. Spots of an absorbing dye were applied to the skin surface in the region of injection site 1. At site 1 cells labeled with PKH26 were injected into the region demarcated: by the red oval and imaged with a standard filter set with 15 seconds exposure. Fluorescence was obliterated in the region where the marker dye was applied, indicating that cells were subcutaneous. At site 2 cells labeled with compound 13 were injected into mouse and imaged with a compound 13 filter set for 6.5 seconds exposure with or without concomitant low intensity background illumination. No PKH26 fluorescence was detected at this site but compound 13 fluorescence was observed. At site 3 cells labeled with compound 15 were injected in the mouse and imaged with a filter set for 40 seconds exposure. No PKH26 or compound 13 fluorescence was detected at this site while compound 15 fluorescence was observed. At site 4 cells labeled with compound 26 were injected into the region demarcated by the yellow oval and imaged with a Filter set for 60 seconds exposure. Both compound 15 and compound 26 fluorescence were detected at this site.

The above description and drawings are only illustrative of a preferred embodiment which achieves the objects, features, and advantages of the present invention, and it is not intended that the present invention be limited thereto. Any modifications of the present invention which come within the spirit and scope of the following claims is considered part of the present invention.

I claim:

1. An in vivo method for assessing the shedding rates of mature surface epithelial cells of a warm blooded animal comprising the steps of:
    labeling mature surface epithelial cells at a target site of the animal with a cyanine dye, and monitoring the site for the presence or absence of the label following said labeling step, wherein the cyanine dye is a compound having the structural formula:

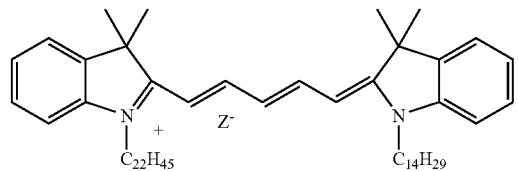

wherein Z is a biologically compatible counterion.

2. A compound having the structural formula

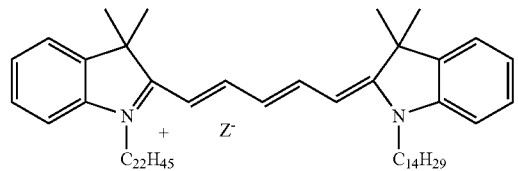

wherein Z is a biologically compatible counterion.

3. An in vivo method for assessing the shedding rates of mature surface epithelial cells of a warm-blooded animal, comprising the steps of:
    labeling mature surface epithelial cells at a target site of the animal with a cyanine dye;
    exciting the target site with a light source; and
    monitoring the site for the presence of absence of fluorescence resulting therefrom;
wherein the cyanine dye is a compound having the structural formula:

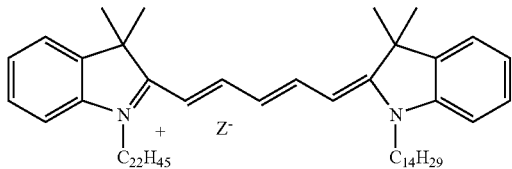

wherein Z is a biologically active counterion.

4. The method of claim 3 wherein the site is a mucosal surface.

5. The method of claim 4 wherein the mucosal surface lines the surface of the gastrointestinal tract, the respiratory tract, or the genitourinary tract.

6. The method of claim 4 wherein the site is a mucosal surface of the stomach.

7. The method of claim 4 wherein the site is a mucosal surface of the colon.

8. The method of claim 3 wherein cell shedding rates are detected by observing changes in the level of the label at the site at a pre-selected time following said labeling step.

9. The method of claim 3 wherein the excitation light has a wavelength of from about 600 nm to about 900 nm.

10. The method of claim 3 wherein the epithelial cells are labeled by direct application of a labeling composition to the site.

11. A method for labeling a cell, comprising the steps of: contacting the cell with a compound having the structural formula:

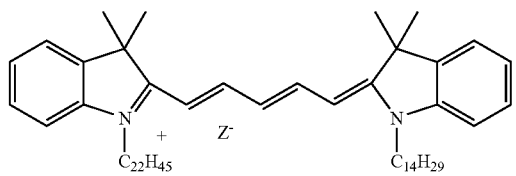

wherein Z is a biologically compatible counterion.

12. The method according to claim 11 wherein said labeling composition comprises a pharmaceutically acceptable vehicle.

* * * * *